US006540684B2

(12) United States Patent
Averkiou et al.

(10) Patent No.: US 6,540,684 B2
(45) Date of Patent: Apr. 1, 2003

(54) ULTRASONIC PERFUSION MEASUREMENT USING CONTRAST AGENTS

(75) Inventors: Michalakis Averkiou, Kirkland, WA (US); Matthew Bruce, Seattle, WA (US); Jeffry E. Powers, Bainbridge Is., WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/007,287

(22) Filed: Nov. 8, 2001

(65) Prior Publication Data

US 2002/0040189 A1 Apr. 4, 2002

Related U.S. Application Data

(62) Division of application No. 09/188,650, filed on Nov. 9, 1998, now Pat. No. 6,315,729, which is a division of application No. 08/723,483, filed on Sep. 27, 1996, now Pat. No. 5,833,613.

(60) Provisional application No. 60/013,950, filed on Mar. 22, 1996, provisional application No. 60/018,095, filed on May 22, 1996, and provisional application No. 60/005,009, filed on Oct. 10, 1995.

(51) Int. Cl.[7] .................................................. A61B 8/06
(52) U.S. Cl. ........................................................ 600/458
(58) Field of Search ................................ 600/437, 443, 600/447, 454–456, 458, 504–505, 507

(56) References Cited

U.S. PATENT DOCUMENTS

| | | | |
|---|---|---|---|
| 4,276,885 A | 7/1981 | Tickner et al. | |
| 4,572,203 A | 2/1986 | Feinstein | |
| 4,718,433 A | 1/1988 | Feinstein | |
| 4,774,958 A | 10/1988 | Feinstein | |
| 5,040,537 A | 8/1991 | Katakura | |
| 5,158,071 A | 10/1992 | Umemura et al. | |
| 5,241,473 A | 8/1993 | Ishihara et al. | |
| 5,255,683 A | 10/1993 | Monaghan | |
| 5,410,516 A | 4/1995 | Uhlendorf et al. | |
| 5,419,328 A | 5/1995 | Goh et al. | |
| 5,425,366 A | 6/1995 | Reinhardt et al. | |
| 5,456,255 A | 10/1995 | Abe et al. | |
| 5,456,257 A | 10/1995 | Johnson et al. | |
| 5,560,364 A | 10/1996 | Rorter | |
| 5,577,505 A | 11/1996 | Brock-Fisher et al. | |
| 5,608,690 A | 3/1997 | Hossack et al. | |
| 5,617,862 A | 4/1997 | Cole et al. | |
| 5,628,322 A | 5/1997 | Mine | |
| 5,685,310 A | 11/1997 | Porter | |
| 5,724,976 A | 3/1998 | Mine et al. | |
| 5,735,281 A | 4/1998 | Rafter et al. | |
| 5,740,128 A | 4/1998 | Hossack et al. | |
| 5,833,613 A | * 11/1998 | Averkiou et al. | 600/440 |
| 6,315,729 B1 | * 11/2001 | Averkiou et al. | 600/458 |

OTHER PUBLICATIONS

Burns et al., "Harmonic Imaging Principles and Preliminary Results," Angiology, vol. 47, No. 7, pt. 2, Jul. 1996, pp. S63=S74.

Burns et al., "Harmonic Power Mode Doppler Using Microbubble Contrast Agents," J.E.M.U., vol. 16, No. 4, 1994, pp. 132–142.

* cited by examiner

Primary Examiner—Francis J. Jaworski
(74) Attorney, Agent, or Firm—W. Brinton Yorks, Jr.

(57) ABSTRACT

Apparatus and methods are disclosed for the detection and imaging of ultrasonic contrast agents. Ultrasonic apparatus is provided for coherent imaging of ultrasonic contrast agents, and for detecting harmonic contrast agents. The inventive apparatus includes a dual display for simultaneously viewing a real time image which displays the location of the contrast agent and a triggered contrast image. Methods of contrast agent detection and imaging include the measurement of perfusion rate characteristics, multizone contrast imaging, multifrequency contrast imaging, tissue perfusion display, and high PRF contrast image artifact elimination.

8 Claims, 12 Drawing Sheets

ULTRASONIC PERFUSION MEASUREMENT USING CONTRAST AGENTS

This a divisional application of U.S. patent application Ser. No. 09/188,650 filed Nov. 9, 1998 now U.S. Pat. No. 6,315,729, which is a divisional application of U.S. patent application Ser. No. 08/723,480, filed Sep. 27, 1996 now U.S. Pat. No. 5,833,613, which claims the benefit of U.S. Provisional Application No. 60/005,009 filed Oct. 10, 1995; Provisional Application No. 60/013,950 filed Mar. 22, 1996; and Provisional Application No. 60/018,095 filed May 22, 1996.

This invention relates to ultrasonic diagnosis and imaging of the body with ultrasonic contrast agents and, in particular, to new methods and apparatus for ultrasonically detecting and imaging with contrast agents.

Ultrasonic diagnostic imaging systems are capable of imaging and measuring the physiology within the body in a completely noninvasive manner. Ultrasonic waves are transmitted into the body from the surface of the skin and are reflected from tissue and cells within the body. The reflected echoes are received by an ultrasonic transducer and processed to produce an image or measurement of blood flow. Diagnosis is thereby possible with no intervention into the body of the patient.

Materials known as ultrasonic contrast agents can be introduced into the body to enhance ultrasonic diagnosis. Contrast agents are substances which strongly interact with ultrasonic waves, returning echoes which may be clearly distinguished from those returned by blood and tissue. One class of substances which has been found to be especially useful as an ultrasonic contrast agent is gases, in the form of tiny bubbles called microbubbles. Microbubbles present a significant acoustic impedance mismatch in the body, and nonlinear behavior in certain acoustic fields which is readily detectable through special ultrasonic processing. Gases that have been stabilized in solutions in the form of tiny microbubbles are infused into the body and survive passage through the pulmonary system and circulate throughout the vascular system. Microbubble contrast agents are useful for imaging the body's vascular system for instance, as the contrast agent can be injected into the bloodstream and will pass through the veins and arteries of the body with the blood supply until filtered from the blood stream in the lungs, kidneys and liver.

One type of microbubble contrast agent currently under investigation comprises coated microbubbles. The microbubbles of the contrast agent are covered with a thin biodegradable coating or shell. The microbubbles have diameters between 0.1 μm and 4.0 μm and a specific density about 1/10 of the density of water. The coated microbubbles are suspended in an aqueous solution for infusion into the blood stream.

Coated microbubbles have the advantage of being stable in the body for a significant period of time, as the shells serve to protect the gases of the microbubbles from diffusion into the bloodstream. The size of the microbubbles is chosen to enable the microbubbles to pass through capillary beds in the body.

At moderately high sound pressure amplitudes the acoustic pressure waves can cause the shells of coated microbubbles to rupture, freeing the bubbles to behave as noncoated microbubbles until they diffuse into the bloodstream. In their noncoated form acoustic energy can induce nonlinear motion of the microbubbles, itself a detectable ultrasonic phenomenon. This acoustically induced destruction and collapse of the microbubbles produces a high amplitude response and a characteristically bright pattern in the color Doppler mode. Hence color Doppler is an advantageous modality for detecting the collapse of contrast agent microbubbles.

U.S. Pat. No. 5,456,257, assigned to the same assignee as the present invention, describes a technique for detecting microbubbles through phase insensitive detection of microbubble destruction and differentiation of the detected signals on a spatial basis. Phase insensitive contrast agent detection advantageously reduces artifacts from moving tissue, and also performs well when imaging contrast agent perfused tissue, where the contrast agent is finely distributed and moving slowly through the fine capillary structure of tissue. It is desirable to be able to perform contrast agent imaging with equal effect in large, rapidly moving blood pools such as the chambers of the heart. It is also desirable to specifically tailor the operation of the ultrasound machine to harmonic characteristics when performing harmonic contrast imaging.

In accordance with the principles of present invention, new and improved apparatus and methods for the detection and imaging of ultrasonic contrast agents are provided. Ultrasonic apparatus is provided for coherent imaging of ultrasonic contrast agents, which is advantageous in blood pool contrast imaging. In a second embodiment, the apparatus is specially tailored to be programmed with response characteristics suitable for harmonic contrast agents. The inventive apparatus also includes a display for simultaneously viewing a real time image which displays anatomical structures for localization of the contrast agent and a triggered contrast image displaying contrast enhanced images. Methods of employing the inventive apparatus with contrast agents include the measurement of perfusion rate characteristics, multizone contrast imaging, a technique for discerning larger vessels in a bed of fine capillary structures, multifrequency contrast imaging, the display of contrast enhanced tissue, and a technique for the elimination of artifacts occurring during high PRF contrast image acquisition.

In the drawings:

FIG. 1 illustrates in block diagram form an ultrasonic diagnostic system of U.S. Pat. No. 5,456,257 which is capable of performing phase insensitive contrast agent detection;

Figure 1:
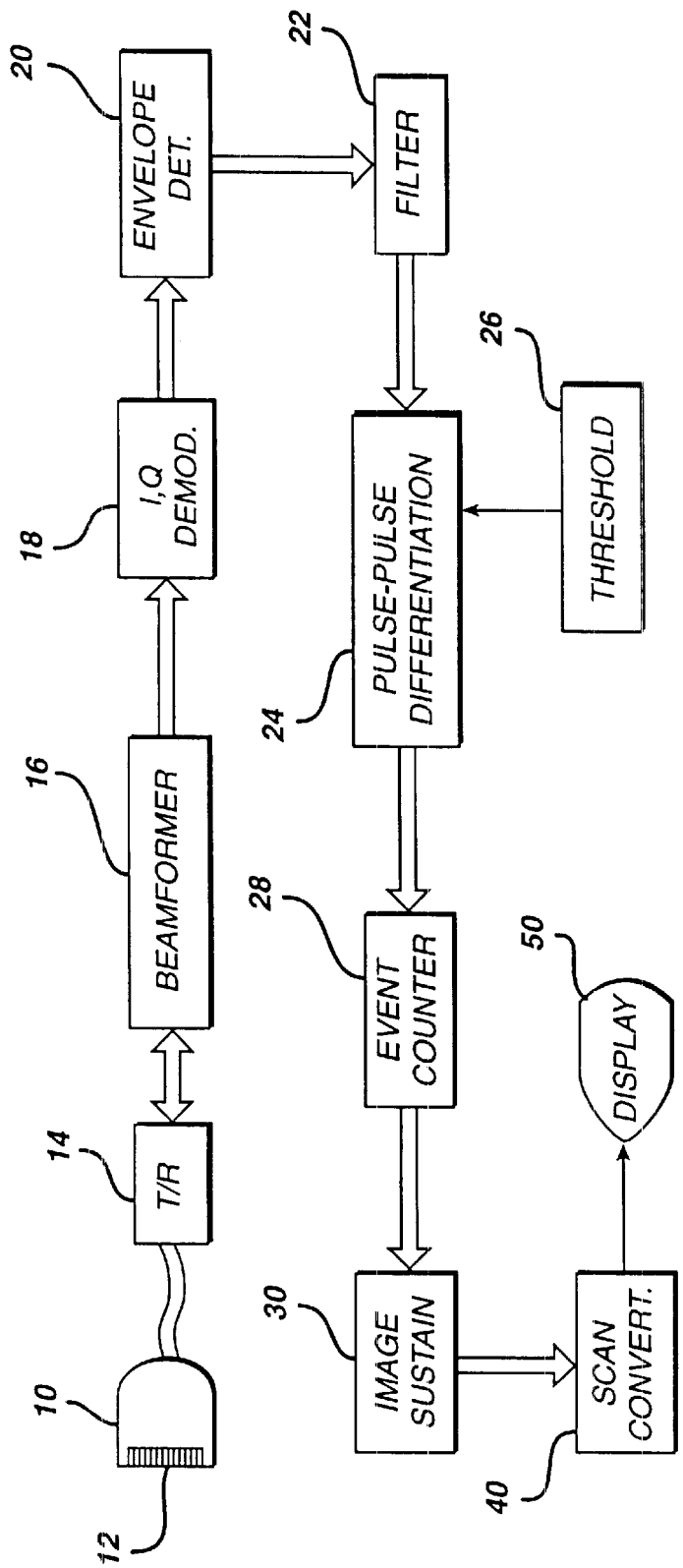

Referring to FIG. 1, an ultrasonic diagnostic system described in U.S. Pat. No. 5,456,257 is illustrated in block diagram form. This ultrasound system is capable of performing phase insensitive contrast agent detection as described in that patent. In the illustrated system, coherent echo signals produced by a beamformer 16 are quadrature demodulated by an I,Q demodulator 18 to produce quadrature I and Q signal components. The demodulated signal components are amplitude detected by an envelope detector 20. The detected signals are filtered by a filter 22 to remove noise and other extraneous signal components. Spatially aligned, temporally separated detected echo signals are differentiated by a pulse to pulse differentiation subsystem 24, and the differential signals are used to form contrast agent enhanced images.

Performing pulse to pulse differentiation of envelope detected echo signals provides advantages in certain procedures. When contrast agents are being used in a mode where microbubbles in the fine capillary structures of tissue are destroyed by ultrasonic waves, differentiation of the echo envelope is particularly useful. In this mode of operation a first ultrasonic pulse destroys the microbubbles in the tissue and these destruction events are received and envelope detected. A second pulse is transmitted to the same locations, and the returning echoes, ideally, show an absence of microbubbles at the locations where the microbubbles were destroyed. The second set of echoes is subtracted from the first set on a spatial basis, yielding difference signals of substantial magnitude at the locations where the microbubbles were destroyed, which are then displayed at corresponding pixel locations on a display. In a realistic setting the second set of echoes may not actually reveal voids where microbubbles were destroyed, due to motional effects, diffusion rates, and other bubble activity. However the difference in bubble activity from one pulse to the next will provide a highly detectable response when differentiated on a pulse to pulse, spatial basis.

This dramatic difference in scattering characteristics of microbubbles from one pulse to another may be due to a host of factors: the bursting of microbubble coatings; oscillation and nonlinear microbubble motion; diffusion of a microbubble during the interpulse interval; or bubble repositioning, for instance. When microbubble destruction is referred to herein it encompasses the effects of phenomena such as these.

Figure 2:
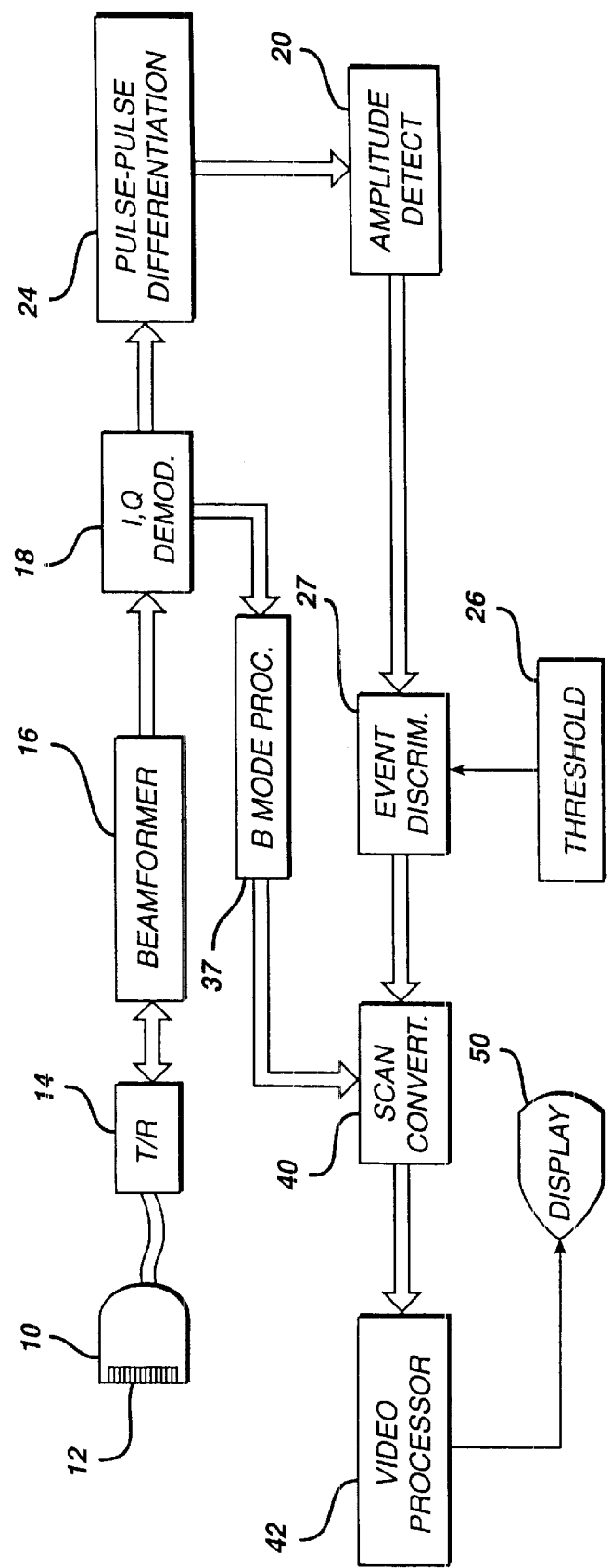
FIG. 2 illustrates in block diagram form an ultrasonic diagnostic system of the present invention which is capable of performing coherent contrast agent detection.

A first embodiment of an ultrasonic diagnostic system constructed in accordance with the principles of the present invention is shown in FIG. 2. This embodiment provides coherent detection of ultrasonic contrast agents. An ultrasonic probe 10 includes an array 12 of ultrasonic transducers which transmit and receive ultrasonic energy. During transmission, an ultrasonic beamformer 16 controls the timing of actuation of the separate elements of the array 12 by activating the transducer pulsers of a transmitter/receiver 14 at appropriate times to pulse the transducer elements so that a steered and focused ultrasonic beam is produced. During reception ultrasonic echoes received by the transducer elements are received by transmitter/receiver 14 and coupled to separate channels of the beamformer 16, where the signals are appropriately delayed then combined to form a sequence of coherent echo signals over the depth of reception in the body of the patient.

The coherent echo signals are quadrature demodulated by an I,Q demodulator 18 which produces quadrature I and Q signal components. The demodulated signal components are coupled to a B mode processor 37 which filters, detects, and maps greyscale echo signals in the usual manner. The greyscale echo signals of the scanlines of an image are coupled to a scan converter 40 for display of a B mode image.

In accordance with the principles of the present invention the I and Q signal components are alternatively (or in addition) coupled to a pulse to pulse differentiation circuit 24 which differentiates echoes received from the same sample volume (location) in the body on a temporal basis. The results of this differentiation are coupled to an amplitude detector 20 and the differential response signals are coupled to an event discriminator 27. The event discriminator discriminates events of microbubble destruction at the sample volume location from the differentiated echo information. One convenient way to perform this discrimination is by comparison of the detected signals to a threshold from threshold generator 26, passing signals above a threshold and rejecting signals below the threshold. The discriminator will detect microbubble destruction events and reject low level noise.

Detected events are coupled to the scan converter 40 for production of a spatial image of the microbubble destruction events in the desired image format. The destruction event image may be shown separately, or may be combined with the B mode image to show the contrast agent in relation to surrounding tissue structure. The images are coupled to a video processor 42 which produces video signals for display on an image display 50.

This coherent contrast agent detection technique is highly sensitive to small variations in microbubble activity in the image area, and performs well when imaging the blood pool of a heart chamber, for instance. In a large blood pool with a large population of moving microbubbles, the probability of differential microbubble activity from one pulse to another is extremely high, explaining the high sensitivity of this technique for heart chamber imaging. In comparison with the incoherent contrast agent detection technique, coherent microbubble detection is more sensitive to tissue motion and more sensitive to individual microbubble events in high contrast agent concentrations. It is also possible to process received echoes both coherently and incoherently, to form an image which contains information from both processes.

Contrast agent detection in accordance with the present invention provides excellent tissue clutter rejection. Microbubble echo signals are generally not received alone, but are usually accompanied by echo signals of much greater amplitude which are returned from neighboring tissue and structures. These tissue echoes can be several orders of magnitude greater than any of the microbubble echo signals, effectively masking them. The pulse to pulse differentiation processing can reject the tissue signals by effectively canceling them, revealing the contrast agent echoes which can then be more readily discriminated. This cancellation is enhanced by high PRF pulses, which further diminishes motional artifacts from tissue.

It has been found that the microbubbles of a contrast agent exhibit greater sensitivity to ultrasonic pulses of certain characteristics and lesser sensitivity to pulses of other characteristics. In general, the higher the amplitude, the lower the frequency, and (to a lesser extent) the longer the burst length, the more sensitive the microbubbles are to destruction. Thus, the time of occurrence of microbubble destruction can be modulated and controlled. Microbubbles can be imaged in the bloodstream by scanning at a high frequency with low amplitude, (and to a lesser extent) short burst length pulses. When it is desired to stimulate microbubble destruction, higher power pulses of lower frequency and longer burst length are transmitted into the bloodstream. The ultrasound system of the present invention is provided with control presets for these two pulse transmission characteristics, enabling the clinician to switch from nondestructive imaging pulses to microbubble destruction pulses when the clinician so desires. The preferred display of anatomical structures and microbubble activity employs programmed switching between the destructive and nondestructive pulse modes for contrast agent and anatomical structure imaging.

Figure 4:
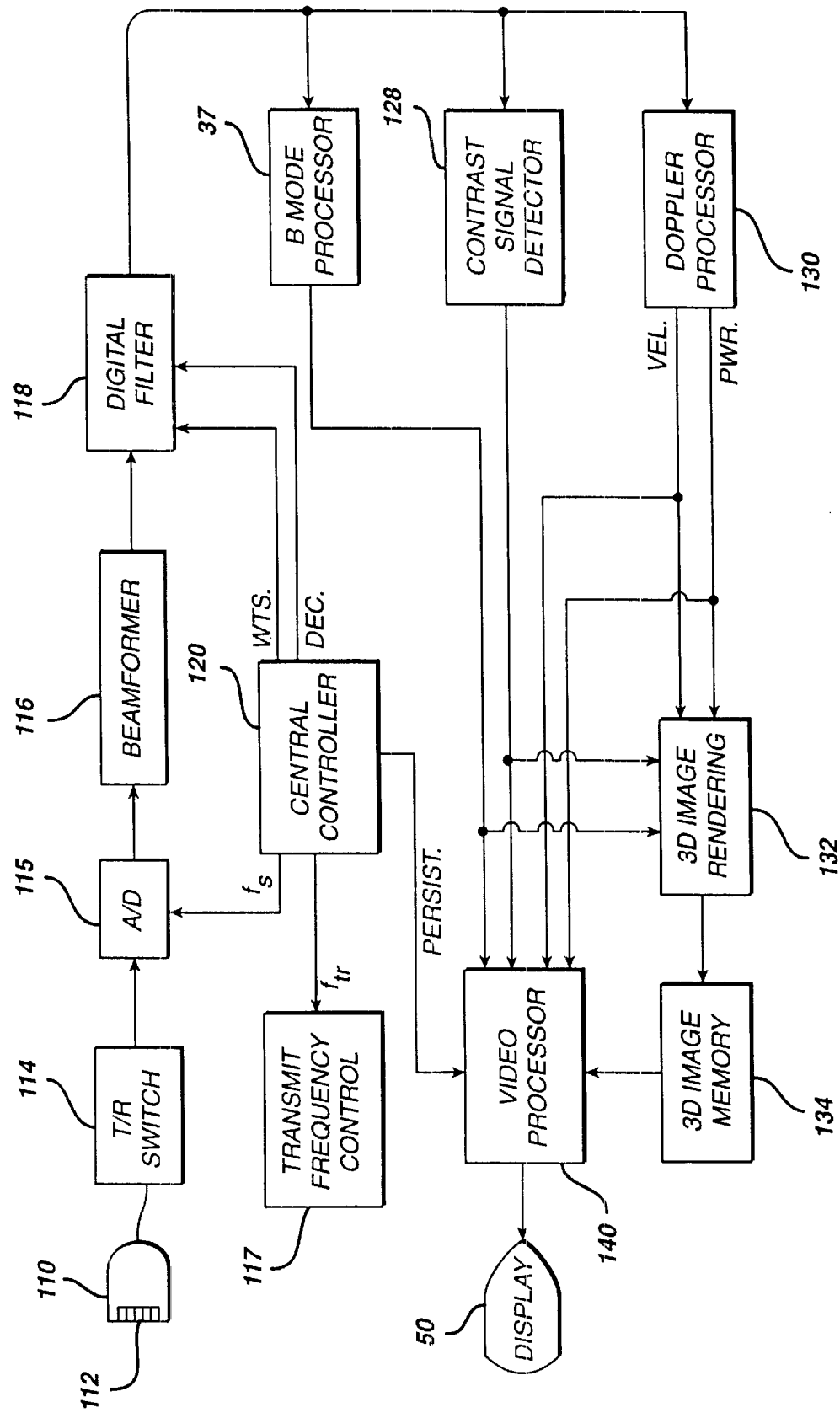
FIG. 4 illustrates in block diagram form a second embodiment of the present invention which provides performance advantages for harmonic contrast agent detection.
Figure 5:
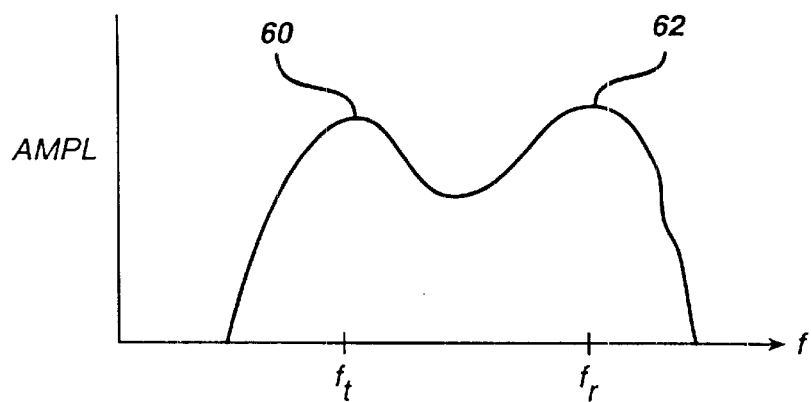
FIGS. 5 and 6 illustrate passband characteristics used to explain the performance of the embodiment of FIG. 4.
Figure 6:
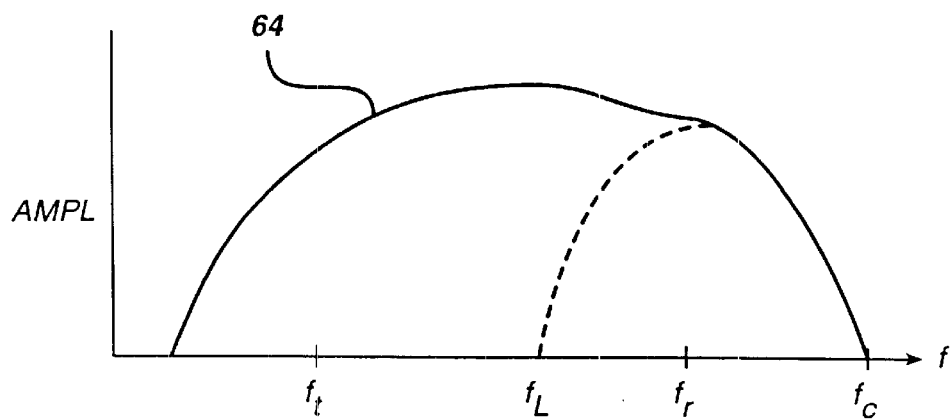

A second embodiment of an ultrasonic diagnostic system constructed in accordance with the principles of the present invention for use with harmonic contrast agents is shown in FIG. 4. In this second embodiment the array transducer 112 of the probe 110 transmits ultrasonic energy and receives echoes returned in response to this transmission. The response characteristic of the transducer can exhibit two passbands, one around the central transmit frequency and another about the center of the received passband. For imaging harmonic contrast agents, a broadband transducer having a passband encompassing both the transmit and receive passbands is preferred. The transducer may be manufactured and tuned to exhibit a response characteristic as shown in FIG. 5, in which the lower hump 60 of the response characteristic is centered about the center transmit frequency $f_t$, and the upper hump 62 is centered about the center frequency $f_r$ of the response is passband. The transducer response characteristic of FIG. 6 is preferred, however, as the single dominant characteristic 64 allows the probe to be suitable for both harmonic contrast imaging and imaging without harmonic contrast agents. The characteristic 64 encompasses the central transmit frequency $f_t$, and also the harmonic receive passband bounded between frequencies $f_L$ and $f_c$, and centered about frequency $f_r$. A typical harmonic contrast agent can have a response such that transmission about a central transmit frequency of 1.7 MHz will result in harmonic returning echo signals about a frequency of 3.4 MHz. A response characteristic 64 of approximately 2 MHz would be suitable for these harmonic frequencies.

Figure 7:
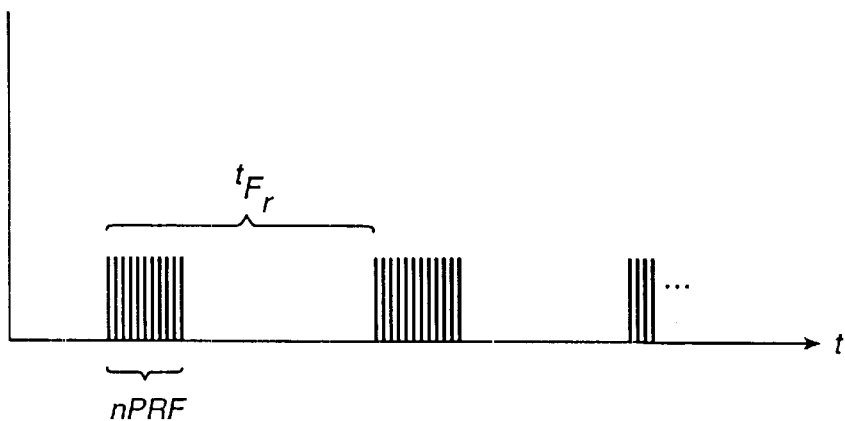
FIG. 7 illustrates the principle of time separated pulsing when imaging contrast agents.

In FIG. 4 a central controller 120 provides a control signal $f_{tr}$ to a transmit frequency control circuit 121 to control the center frequency and time of transmission of the transmitted ultrasonic energy. The transmit frequency control circuit pulses the elements of the transducer array 112 by means of a transmit/receive switch 114. A preferred method of pulsing the transducer array is in bursts which scan with sufficient pulses to form an image, followed by intervals of no pulse transmission. Such bursts and intervals are shown in FIG. 7, which shows a burst interval nPRF and a frame interval $t_{Fr}$, the frame interval including the burst interval and an interval of no pulse transmission. The latter interval allows time for new contrast agent coursing through the body to infuse the vessels and tissue of the image plane between frame bursts. The frame intervals can be on the order of one second, and can be gated to the heart rate or asynchronous with respect to the heart rate. During each nPRF burst interval, echoes from the same spatial locations can be gathered for Doppler processing. Preferably a high PRF rate such as 6 KHz is used. Imaging procedures of this type are the subject of U.S. Pat. Nos. 5,685,310 and 5,560,364.

Medical diagnostic ultrasonic scanning is limited by regulatory requirements in the peak pressure amplitude of a transmitted pulse and the integral of the energy transmitted. The preferred scanning of contrast agents in accordance with the embodiment of FIG. 4 utilizes relatively high peak pulse power, with the time integral of transmitted energy lessened by the intervals during which no pulses are transmitted. The ultrasound system is set to operate with a relatively high mechanical index and an SPTA moderated by the gated or interval bursts.

Echoes received by the transducer array 112 are coupled through the T/R switch 114 and digitized by analog to digital converters 115. The sampling frequency $f_s$ of the A/D converters 115 is controlled by the central controller. The desired sampling rate dictated by sampling theory is at least twice the highest frequency $f_c$ of the received passband and, for the preceding exemplary frequencies, might be on the order of at least 8 MHz. Sampling rates higher than the minimum requirement are also desirable.

Figure 8:
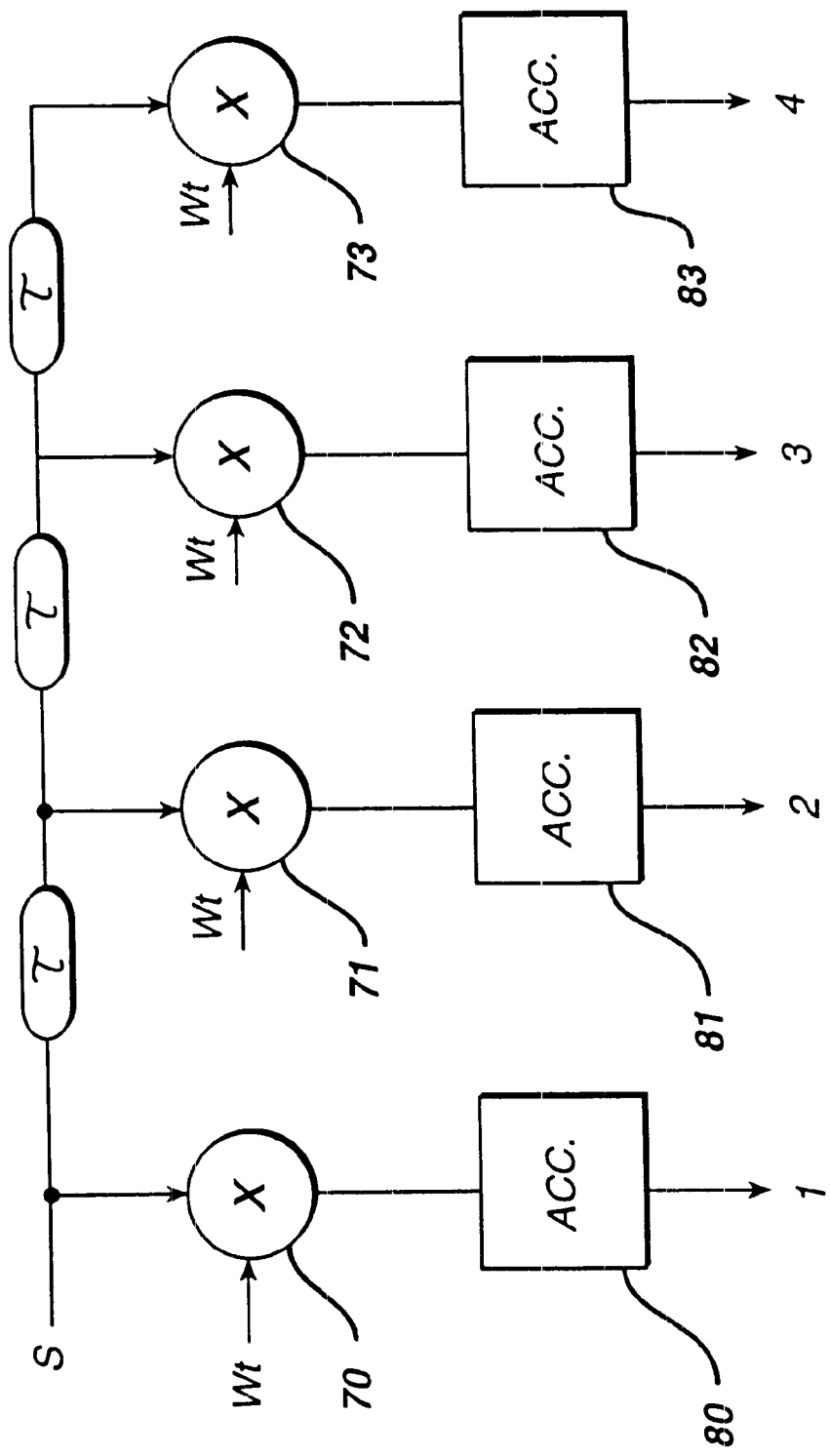
FIG. 8 illustrates an FIR filter structure suitable for use in the embodiment of FIG. 4.

The echo signal samples from the individual transducer elements are delayed and summed by a beamformer 116 to form coherent echo signals. The digital coherent echo signals are then filtered by a digital filter 118. In this embodiment, the transmit frequency $f_t$ is not tied to the receiver, and hence the receiver is free to receive a band of frequencies which is separate from the transmitted band. The digital filter 118 bandpass filters the signals in the passband bounded by frequencies $f_L$ and $f_c$ in FIG. 6, and can also shift the frequency band to a lower or baseband frequency range. The digital filter could be a filter with a 1 MHz passband and a center frequency of 3.4 MHz in the above example. A preferred digital filter is a series of multipliers 70–73 and accumulators 80–83 as shown in FIG. 8. This arrangement is controlled by the central controller 120, which provides multiplier weights and decimation control which control the characteristics of the digital filter. Preferably the arrangement is controlled to operate as a finite impulse response (FIR) filter, and performs both filtering and decimation. For example, only the first stage output 1 could be controlled to operate as a four tap FIR filter with a 4:1 decimation rate. Temporally discrete echo samples S are applied to the multiplier 70 of the first stage. As the samples S are applied, they are multiplied by weights provided by the central controller 120. Each of these products is stored in the accumulator 80 until four such products have been accumulated (added). An output signal is then produced at the first stage output 1. The output signal has been filtered by a four tap FIR filter since the accumulated total comprises four weighted samples. Since the time of four samples is required to accumulate the output signal, a 4:1 decimation rate is achieved. One output signal is produced for every four input samples. The accumulator is cleared and the process repeats. It is seen that the higher the decimation rate (the longer the interval between output signals), the greater can be the effective tap number of the filter.

Alternatively, temporally separate samples are delayed by delay elements τ and applied to the four multipliers 70–73, multiplied, and accumulated in the accumulators 80–83. After each accumulator has accumulated two products, the four output signals are combined as a single output signal. This means that the filter is operating as an eight tap filter with a 2:1 decimation rate. With no decimation, the arrangement can be operated as a four tap FIR filter. The filter can also be operated by applying echo signals to all multipliers simultaneously and selectively time sequencing the weighting coefficients. A whole range of filter characteristics are possible through programming of the weighting and decimation rates of the filter, under control of the central controller.

Returning to FIG. 4, filtered echo signals from tissue, generally filtered by a passband centered about or demodulated from the transmit frequency, are coupled to a B mode processor 37 for conventional B mode processing. Filtered echo signals of the contrast agent passband are coupled to a contrast signal detector 128 which eliminates stationary tissue signals by pulse to pulse subtraction of temporally discrete echoes from a given spatial location, amplitude or envelope detects the resulting difference signals, and discriminates for motion signal components on an amplitude basis. Simple two pulse subtraction of the form $P_1-P_2$ may be employed where $P_1$ represents the echoes received following one pulse and $P_2$ represents the echoes received following another pulse. Three pulse subtraction of the form $|P_1-P_2|+|P_2-P_3|$ may be employed to accumulate more signals from successive bubble destruction pulses.

The filtered echo signals from the digital filter 118 are also coupled to a Doppler processor 130 for conventional Doppler processing to produce velocity and power Doppler signals. The outputs of these processors are coupled to a 3D image rendering processor 132 for the rendering of three dimensional images, which are stored in a 3D image memory 134. Three dimensional rendering may be performed as described in U.S. Pat. No. 5,720,291, and in U.S. Pat. Nos. 5,474,073 and 5,485,842, the latter two patents illustrating three dimensional power Doppler ultrasonic imaging techniques. The signals from the contrast signal detector 128, the processors 37 and 130, and the three dimensional image signals are coupled to a video processor 140 where they may be selected for display on an image display 50 as dictated by user selection. The video processor preferably includes persistence processing, whereby momentary intensity peaks of detected contrast agents can be sustained in the image. One technique for providing persistence is through frame averaging, whereby new image frames are combined with previous frame information on a spatial basis. The combination can be done by weighting the contributions of the old and new frame information and the frame information can be combined in a recursive manner; that is, old frame information is fed back for combining with new frame information. A preferred persistence technique is the fast attack, slow decay technique described in U.S. Pat. No. 5,215,094, which can be applied to both Doppler and contrast agent images.

Several imaging formats have been found to be preferred for contrast imaging. Power motion imaging as described in U.S. Pat. No. 5,718,229 in which the intensity of signals resulting from moving tissue is displayed, has been found to be highly diagnostic for structures such as the walls of the heart when perfused with contrast agents. Power Doppler imaging has been found to yield excellent results for bloodflow. Three dimensional power Doppler imaging of vessels infused with contrast agent provide excellent visualization of the continuity of bloodflow and stenoses. The combination of B mode or power motion structural information with power Doppler signals in accordance with the semitransparent rendering techniques of the aforementioned U.S. Pat. No. 5,720,291 provides superb renderings of both flow and surrounding structure.

Figure 3:
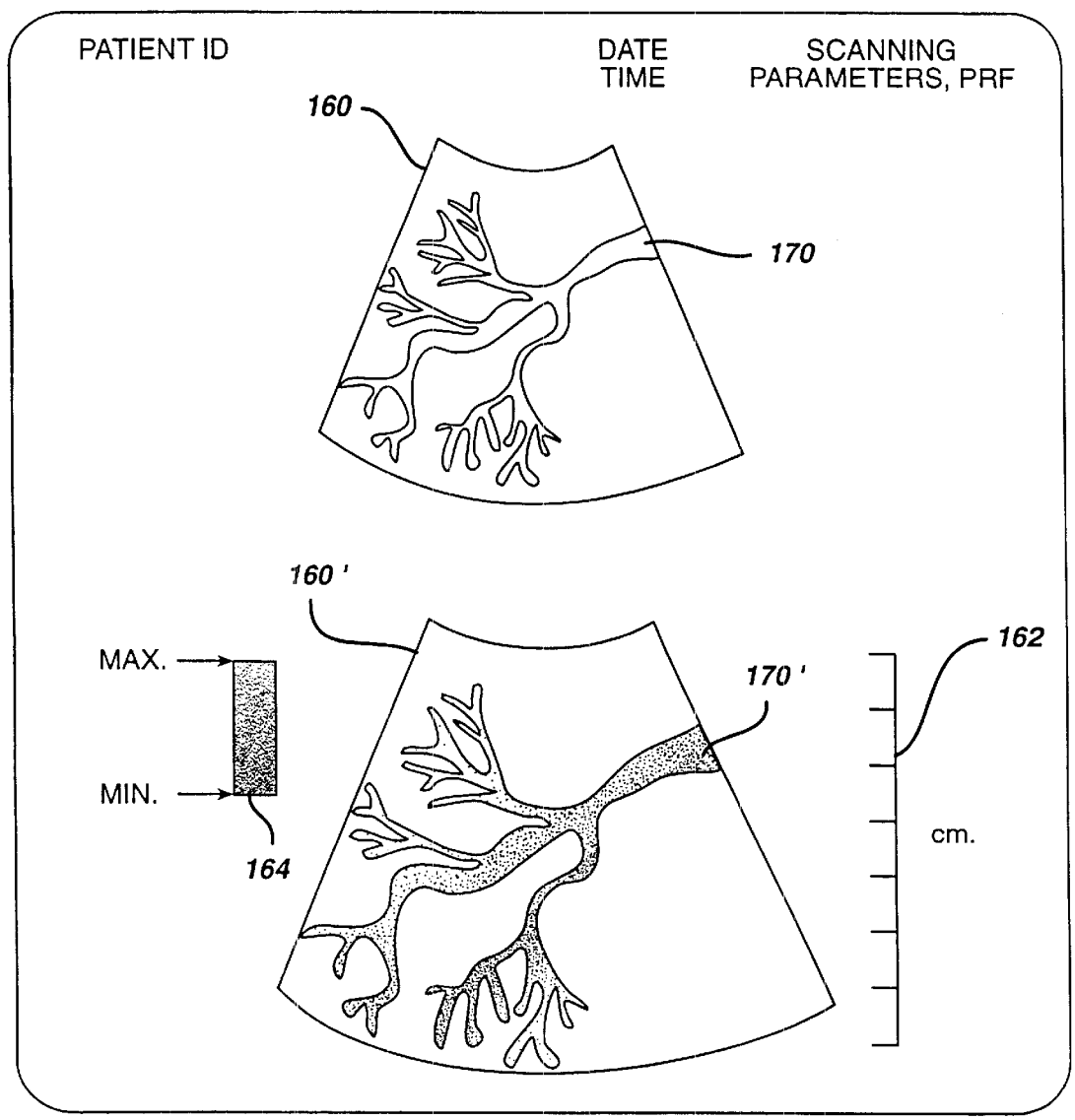
FIG. 3 illustrates an ultrasonic image display for contrast agent imaging.

A preferred display format for contrast agent imaging is depicted by the screen display of FIG. 3. In this display the signals produced by the B mode processor 37 are used to display a real time image display 160 of structure in the body such as a blood vessel 170. This real time image is used by the clinician to ascertain and locate the area of the body to be imaged. Preferably the B mode image is created from echoes returning from nondestructive ultrasonic imaging pulses. As discussed above, pulses of low amplitude, high frequency, and short burst duration will generally not destroy the microbubbles. However, echoes from pulses destructive of microbubbles are used by the contrast signal detector 128 to produce contrast agent images 160' on the same or an adjacent monitor. Preferably the contrast agent images 160' are triggered to be acquired at a predetermined phase of the heart cycle, using a heart gate triggering from the phases of the heartbeat waveform. When the heartbeat is at the desired phase of its cycle, a burst of relatively high amplitude, low frequency, long burst duration pulses are transmitted to destroy the microbubbles in the image plane and detect and display those events. A B mode image acquired at or near the same heartbeat phase is displayed, with the vessel or organ 170' filled in with the imaged microbubble destruction events. Thus, the display screen of FIG. 3 will show a B mode image 160' in real time, and a contrast agent image 160' which is updated each heart cycle.

While the foregoing image presentation is especially useful in cardiology where the beating heart is constantly in motion, a variation of this presentation is especially useful in radiology where tissue structure is more stationary. In the variation, a real time B mode image 160' of anatomical structure is shown, with fluid flow 170' filled in with color Doppler. This real time color flow Doppler image is then periodically filled in with detected contrast agent, sharply illuminating the bloodflow. The colorflow Doppler display and the contrast agent display, both of which are filling in the same areas of the anatomical display, may be shown in the same, similar, or contrasting colors and intensities. The periodicity of the overlaid contrast agent display may be synchronized to the heart cycle with an EKG trigger as described above, or the periodicity may be chosen by the user and asynchronous to the heart cycle.

Figure 9A:
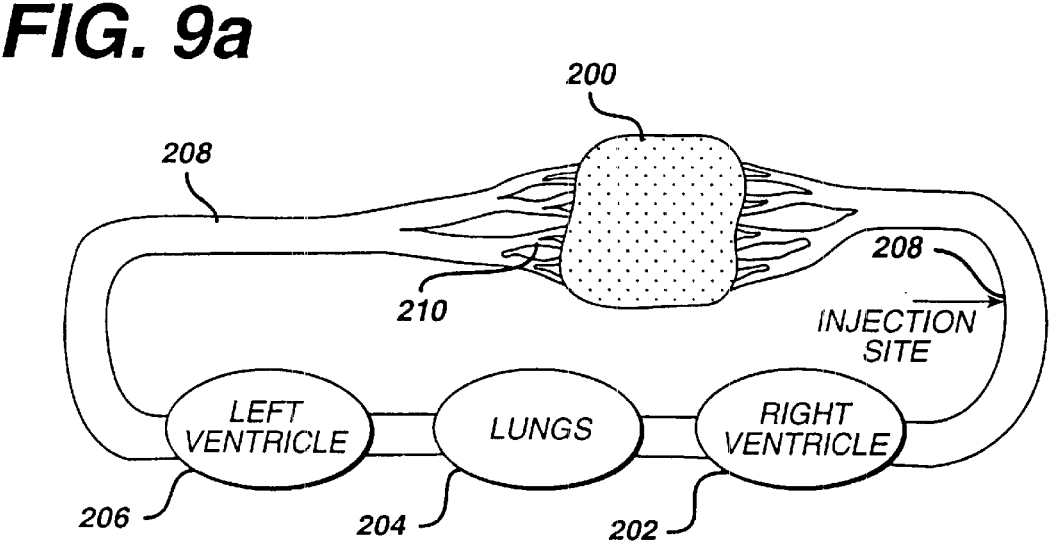
FIGS. 9a–9d illustrate the effects of stenoses on contrast agent perfusion.

A contrast agent procedure which is advantageously performed in accordance with the present invention is the measurement of the rate of perfusion of an organ or area of the body. FIG. 9a illustrates the travel of an intravenous injection of contrast agent to a capillary bed 200. The agent travels in the bloodstream as it moves from the injection site 208 and traverses the right ventricle 202, the lungs 204, and the left ventricle 206 before reaching an artery 209. The contrast agent then begins to infuse the tissue of the capillary bed 200 as blood flows from the artery 200 through the arterioles 210 and into the capillaries of the tissue.

Figure 9B:
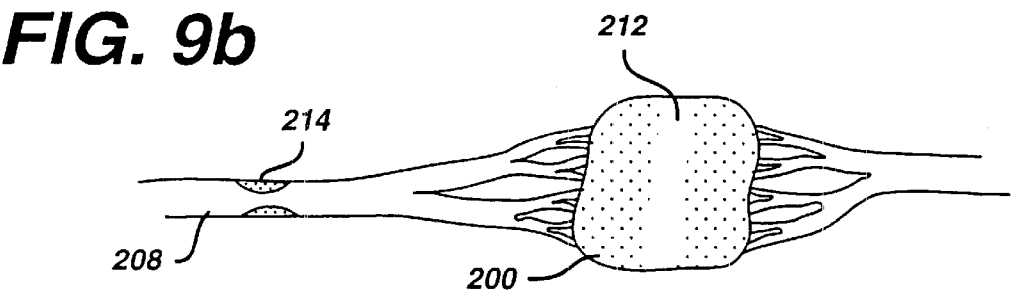
Figure 9C:
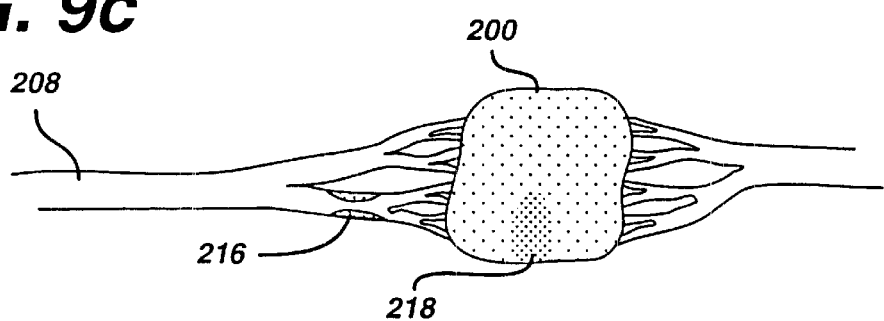
Figure 10A:
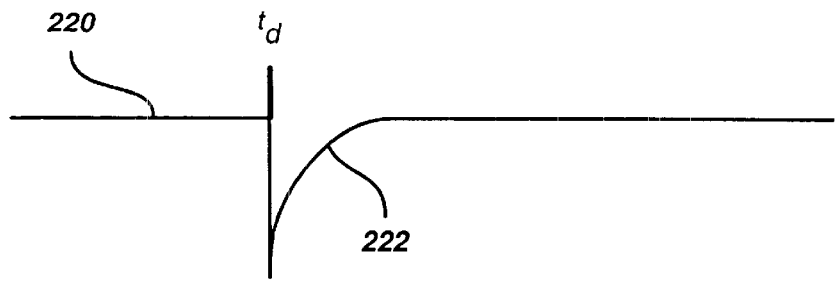
FIGS. 10a and 10b illustrate perfusion curves for good and poor perfusion rates.

The perfusion rate into the capillary bed can be used to evaluate the viability of bloodflow in that region of the body or to identify the location of a stenosis. Ultrasonic pulses are transmitted to destroy microbubbles in a region 212 across the capillary bed 200, as shown in FIG. 9b. If a stenosis 214 is impeding the flow of blood in the artery 209 and hence to the entire capillary bed 200, the rate of reperfusion of microbubbles will be slow across the entire region 212. But if the stenosis 216 is in an artery which feeds only part of the capillary bed 200, the rate of perfusion will be slow in only the portion 218 of the region which is fed through the stenotic artery. This difference in the rate of reperfusion is illustrated graphically by the curves of FIGS. 10a and 10b. Each of these curves shows the same blood volume and hence the same initial microbubble concentration 220 before the microbubbles are destroyed in the capillary bed. At time $t_d$ ultrasonic pulses destroy the microbubbles as indicated by the vertical spike in each curve. When blood is flowing freely into the capillary bed, a rapid rate of reperfusion of microbubbles occurs as indicated by curve 222 in FIG. 10a.

Figure 10B:
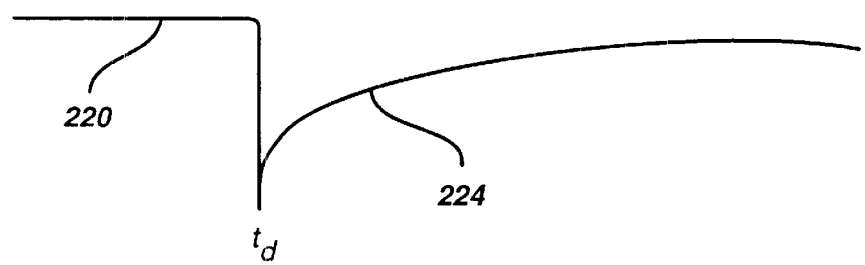
Figure 11A:
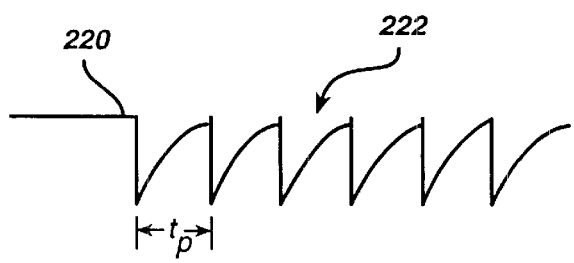
FIGS. 11a and 11b illustrate repetitive perfusion curves for good and poor perfusion rates.
Figure 11B:
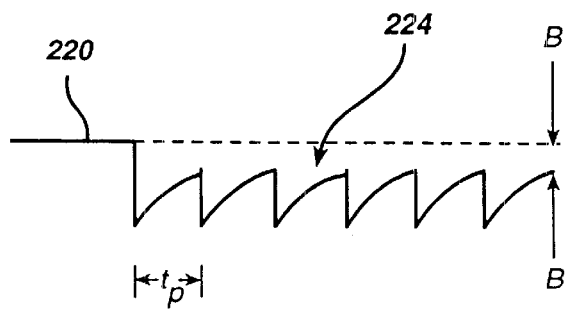

The curve 222 rapidly rises back to the stable microbubble concentration level 220. But when the bloodflow is impeded, the rise of the curve 224 is much more gradual, as indicated in FIG. 10b. The reperfusion curve can be repeated continually as shown by FIGS. 11a and 11b. FIG. 11a shows a repetitive sequence of reperfusion curves 222, each returning to the full perfusion level 220 in a period of time $t_p$. In FIG. 11b, each curve 224 of the same duration $t_p$ is short of the full perfusion level 220 by an amount indicated by arrows B—B.

Figure 13:
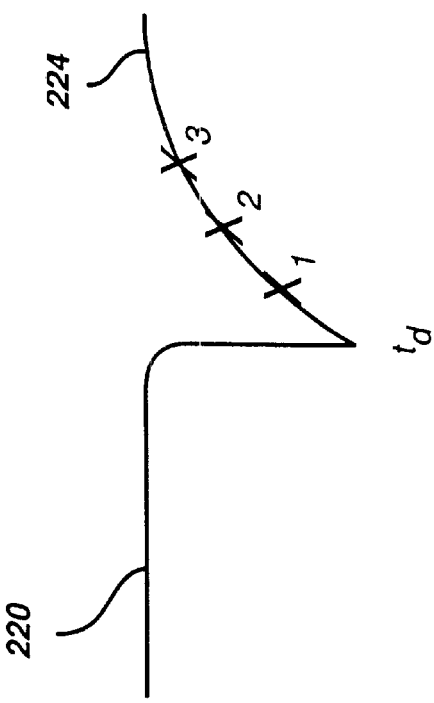
FIG. 13 illustrates a reperfusion curve.

The reperfusion curve may be reproduced as indicated in FIG. 13. Ultrasonic pulses are transmitted at time $t_d$ to destroy the microbubbles in the capillary bed. A short time later pulses are transmitted again, the echoes received and imaged to this time measure the degree of microbubble reinfusion, either by destroying reinfused microbubbles and recording the destruction events, or by counting or integrating pixels in the area which show reinfused microbubbles. The measure of the number of microbubbles reinfused to the region is plotted as a point X of the curve 224. Nondestructive pulses can be repetitively transmitted and echoes received to plot a sequences of X points on the curve as shown in FIG. 13.

Figure 12:
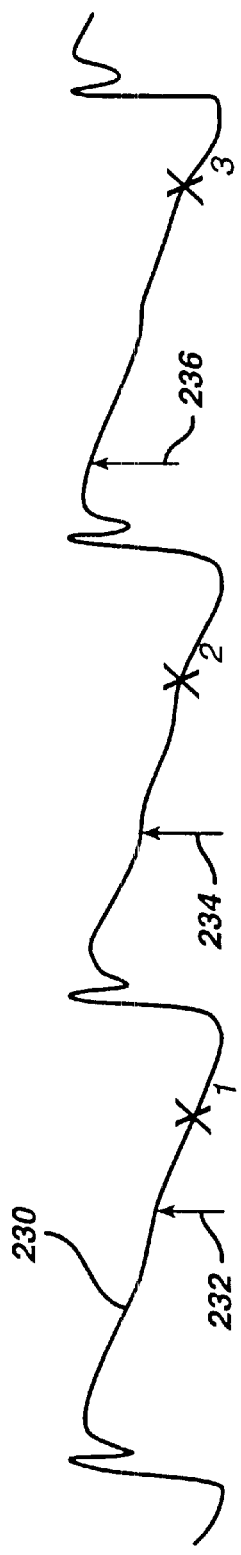
FIG. 12 illustrates a triggering technique for estimating the perfusion curve of FIG. 13.

Another way to measure the X points on the reinfusion curve through readily detectable microbubble destruction events is to utilize a cyclic measure similar to the repetitive pattern of FIG. 11b. The cyclic measure is useful where the flow in the region is strongly pulsatile due to the heartbeat cycle. FIG. 12 shows a heart cycle waveform 230, indicating the pulsatile action of bloodflow. At the peaks of the waveform 230, new blood is pumped into regions of the body during the systolic phase of the heart cycle. Advantage is taken of this reinfusing action by repetitively measuring the degree of contrast agent reinfusion at a constant point in the heart cycle, but following continually differing phases of microbubble destruction. In FIG. 12 the X points of reinfusion measurement all occur at the same phase of the heart cycle. The X points are preceded by changing times at which the microbubbles are destroyed, as indicated by arrows 232, 234, and 236, which successively precess to earlier times in the heart cycle. This means that each $X_n$ point of FIG. 12 will be a later $X_n$ point on the curve 224 of FIG. 13. Since the purpose of ultrasonic transmission at the times of arrows 232, 234, and 236 is to destroy the microbubbles, it is not necessary to receive and analyze the returning echoes at these times. Echo reception and analysis is done at the times of the Xs, and the Xs shown in FIG. 12 can be plotted as the successive Xs in FIG. 13 due to the precession of the destruction time phases indicated by the arrows.

For cardiac imaging it may be desirable to trigger the $X_n$ times in synchronization with the diastolic phase of the heart cycle when the coronary arteries are reinfused with blood. Triggered or gated acquisition is especially significant in cardiac imaging to reduce tissue motion artifacts stemming from the beating movement of the heart.

Figure 9D:
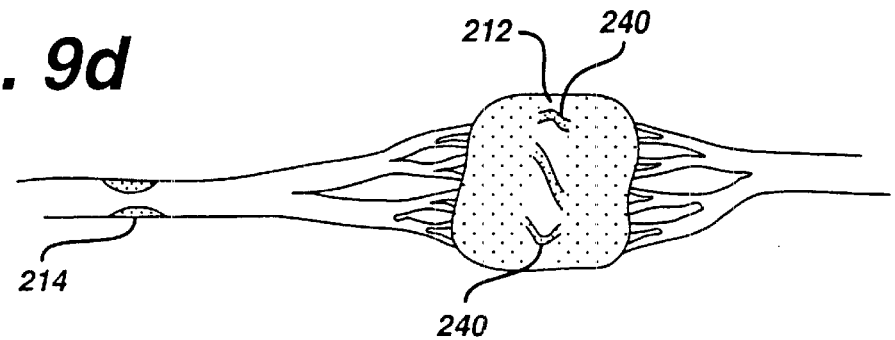

This technique of measuring perfusion by microbubble destruction can also be used to image the flow in major vessels of a capillary bed. In FIG. 9d, for instance, it is seen that the major vessels 240 reinfuse earlier than the fine capillaries in a microbubble depleted region 212. The major vessels 240 can be revealed by detecting microbubbles in the region 212 shortly after pulses have destroyed all of the microbubbles in the region, at which time only the major vessels 240 have been significantly reinfused with contrast agent.

Figure 14A:
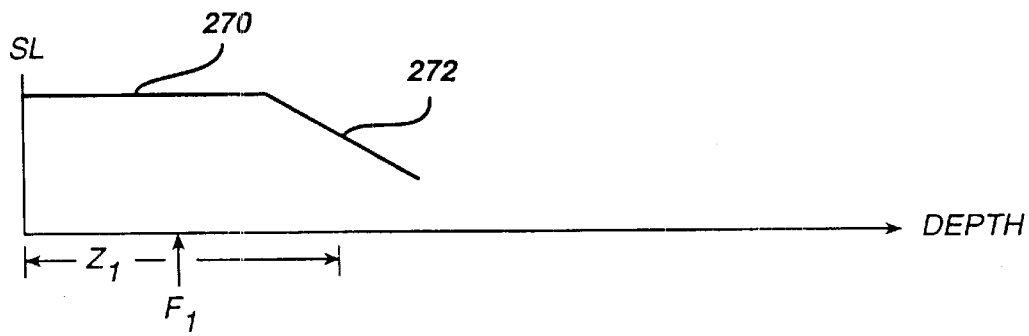
FIGS. 14a–14c illustrate a multizone contrast agent scanning technique.
Figure 14B:
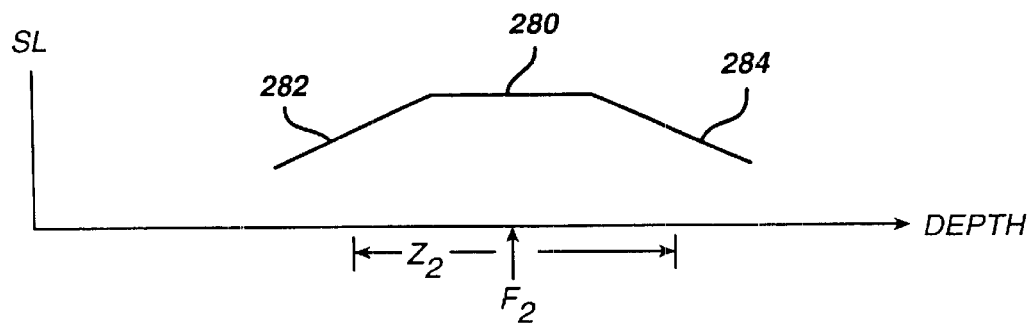
Figure 14C:
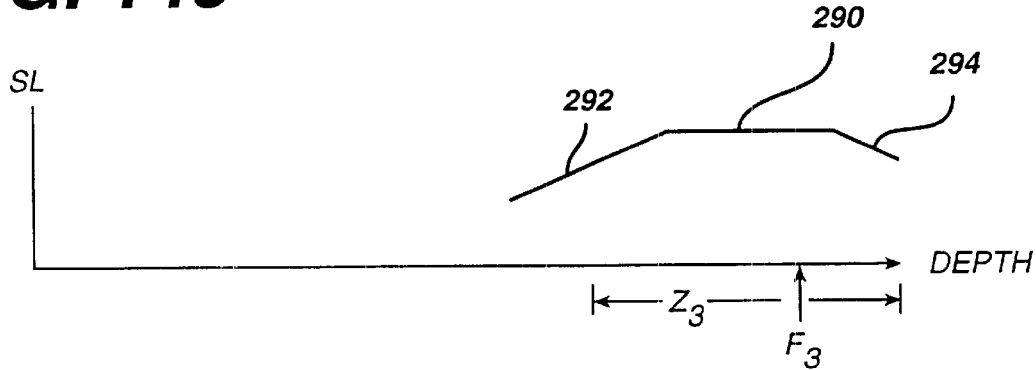

It has been found that it is at times not possible to destroy all microbubbles in the image plane due to several factors. Since microbubbles are destroyed by high energy, focused ultrasound beams tend to destroy more microbubbles near the beam focal point than at other locations. Also, when a dense concentration of microbubbles is to be destroyed, a great deal of the ultrasonic pulse energy is attenuated by the near field microbubbles, leaving insufficient energy to destroy far field microbubbles. A technique for overcoming these effects is shown in FIGS. 14a–14c. In these drawings, the horizontal axis represents depth into the body, with the skin line SL indicated at the left side of each drawing. A typical ultrasonic image may show the skin line at the top of the image and the deepest penetration into the body at the bottom of the image. To bring a maximum level of energy to bear on the microbubbles in the image plane, focused pulses are transmitted to focus the ultrasonic energy on the microbubbles which are to be destroyed. When imaging is to be done to a significant depth in the body, the pulses will not be focused over the full image depth, but will come into focus around a particular focal point and then diverge at greater depths. This is indicated in FIG. 14a, where a transmitted pulse is focused at a focal point $F_1$ which is in a focal zone $Z_1$.

Above this first focal zone $Z_1$ is a line 270, which represents complete microbubble destruction over this near field part of the focal zone $Z_1$ and about the focal point $F_1$. Beyond the focal point the degree of microbubble destruction decreases, as indicated by the declining line 272. These lines are shown as straight lines for ease of explanation; it will be understood that the effect will usually be continually changing and that actual effects may follow a curved relationship.

FIG. 14a represents the transmission of a first pulse along a given beam direction, a result of which is that near field microbubbles are destroyed as indicated by lines 270 and 272. Following this microbubble destruction, a second pulse is transmitted to gather echoes from along the microbubble depleted beam direction. The echoes from the two pulses may be differentiated and displayed using the ultrasonic apparatus of FIGS. 1, 2, or 4.

The next pulse transmission for microbubble destruction is focused at a second focal point $F_2$ in a second focal zone $Z_2$ of the beam. The transmitted pulse energy will readily reach the second focal zone, since the microbubbles in the nearer first zone were previously destroyed. FIG. 14b illustrates this transmission to the second focal zone. Line 282 indicates that the remaining microbubbles at the end of the first zone and the beginning of the second will be destroyed by the second destruction pulse, as will microbubbles around the focal point as indicated by line 280. Beyond the second focal point $F_2$ the degree of microbubble destruction will decline as pulse energy declines, as indicated by line 284. A second interrrogation pulse may be transmitted following the second destructive pulse to differentially detect the second sequence of microbubble destruction events.

Similarly, a third destruction pulse is transmitted along the beam direction, focused at the deepest focal point $F_3$ in the deepest focal zone $Z_3$. The pulse energy readily reaches the third focal zone due to the earlier depletion of microbubbles at shallower depths. The third destruction pulse destroys the remaining microbubbles between the second and third zones as indicated by line 292 in FIG. 14c, destroys microbubbles around the focal point as indicated by line 290, and destroys a decreasing amount of microbubbles beyond the focal point $F_3$ as indicated by line 294. A third interrogation pulse follows for differential detection of the microbubble destruction events in and around zone $Z_3$.

In practice it has been found that peak microbubble destruction is not centered exactly about the focal point axially, but in a depth region just prior to the focal point. This factor should be taken into consideration when considering the placement and overlap of multizone microbubble destruction regions.

The detected destruction events over the three zones are then combined in accordance with the expression $$|P_{F1}-P'_{F1}|+|P_{F2}-P'_{F2}|+|P_{F3}-P'_{F3}|$$

where $P_{Fn}$ represents echoes following a destructive pulse transmission to a given focal zone and $P'_{Fn}$ represents the echoes from a subsequent interrogation pulse. The echoes from each focal zone are spliced together to form a complete image line to the maximum depth of the image. In a preferred embodiment, instead of just detecting microbubble destruction events over the given focal zone, the technique conventionally used in multizone focus imaging, echoes are detected over the full depth following each pulse. This enables the recording of microbubble destruction events outside the given focal zone, providing the greatest detection of destruction events. Thus, each pulse echo pair contains a line of echoes over the full image depth, which are then combined to record the maximum number of microbubble destruction events for the full image line.

It is also seen that, instead of transmitting a pair of pulses to interrogate each focal zone, the echoes returned from later focal zone transmissions can be combined with earlier echoes to differentially detect destruction events. That is, the first term of the above expression could be $|P_{F1}-P_{F2}|$, for instance. However, the use of pulse pairs for each focal zone is preferred, as the aperture changes accompanying focal zone changes can deleteriously affect the precision of the technique.

More uniform, artifact-free multizone microbubble destruction images can be obtained by pulsing nonadjacent beams with time successive pulses. This ensures that each line of microbubbles will be approximately uniformly undisturbed at the beginning of the multizone sequence, preventing successions of bright and dim lines in the ultrasonic image.

Figure 15A:
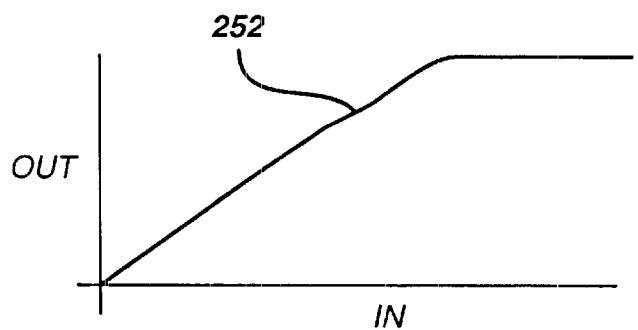
FIGS. 15a and 15b illustrate display mapping characteristics for contrast agent imaging.
Figure 15B:
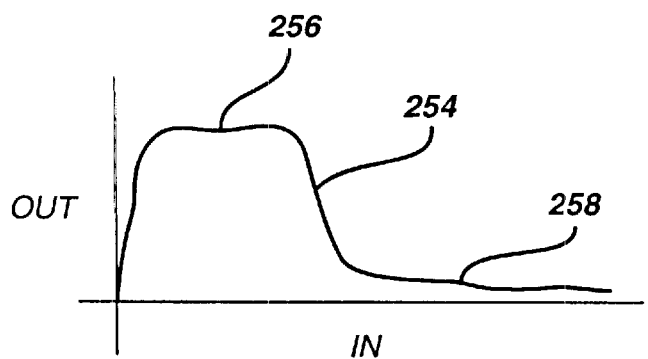
Figure 16:
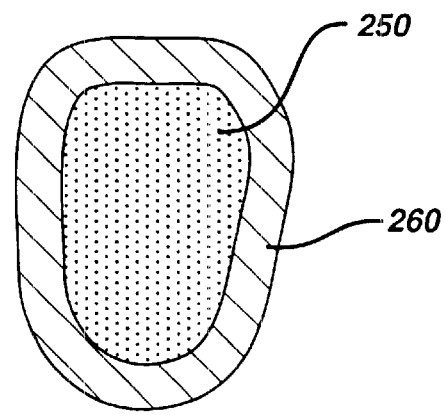
FIG. 16 illustrates the heart in cross section.

FIGS. 15a, 15b and 16 illustrate a preferred technique for displaying contrast agent enhanced images when tissue perfusion is being observed. FIG. 16 illustrates a cross sectional view of the heart, including the myocardium 260 and the blood pool 250 within a chamber of the heart. When a contrast agent has been introduced into the bloodstream, a great quantity of the agent will be contained within large blood pools such as the heart chambers and major vessels, while only a relatively small quantity of contrast agent will enter tissue and organs by way of capillary structures. In the heart image of FIG. 16, a large quantity of contrast agent will be present in the blood pool 250 while a lesser amount will be infused by capillary flow into the myocardium 260.

A conventional ultrasonic display of the cross sectional image of FIG. 16 will cause pixels of greater signal level to be illuminated with greater brightness or color. A typical display mapping characteristic which provides this result is shown in FIG. 15a by mapping characteristic 252. As detected pixel values increase, the display pixels are shown with increasing brightness or color until reaching a maximum plateau level. As a result, the blood pool area 250 in FIG. 16 will be shown brightly or highly colored, whereas the myocardium 260 will be only dimly illuminated or colored.

When the myocardium is the area of interest in FIG. 16, a display mapping characteristic such as that shown in FIG. 15b is employed. The curve 254 in this drawing is seen to begin at a zero level to suppress noise in the image, then rises to a high level 256. Thereafter it declines to a level 258 for higher detected signal values. As a result, lower detected pixel values will be mapped to brightly illuminated or colored display pixels, and higher detected pixel values will be mapped to more dimly illuminated or colored display pixel values. As a consequence of this mapping, the myocardium 260 in FIG. 16 will be brightly illuminated or colored, while the central blood pool is only dimly colored or illuminated. This emphasis provides highlighting of contrast agent perfused tissue over blood pool areas.

Pulse transmission techniques can afford further improvement in contrast agent destruction and detection. While the exact physical mechanisms caused the by interaction of microbubbles with acoustic energy are quite complex, the sizes of microbubbles have an effect upon their destruction at certain frequencies. Since a microbubble contrast agent is often comprised of microbubbles of a wide range of diameters, microbubble destruction events can be increased by transmitting a chirp or multifrequency pulse. By transmitting a frequency modulated pulse, the probability of transmitting destructive energy for a greater range of microbubble sizes is increased. In addition, by modulating both the frequency and amplitude of the destructive pulse, both microbubble destruction and controlled oscillation can be induced. The initial high amplitude, low frequency period of the pulse, followed by a lower amplitude, higher frequency period can induce microbubble shell destruction followed by oscillation of the released microbubble.

Figure 17A:
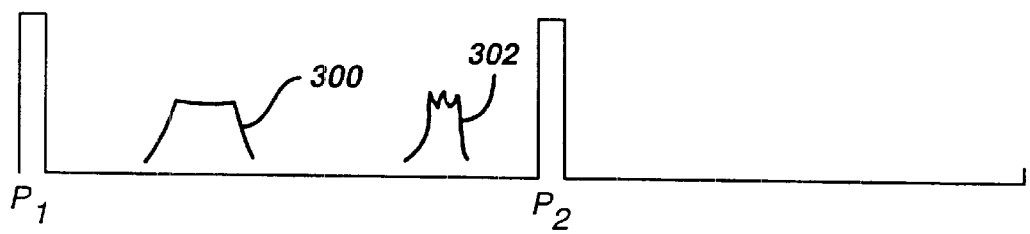
FIGS. 17a–17c illustrate the removal of artifacts occurring during high PRF contrast imaging.
Figure 17B:
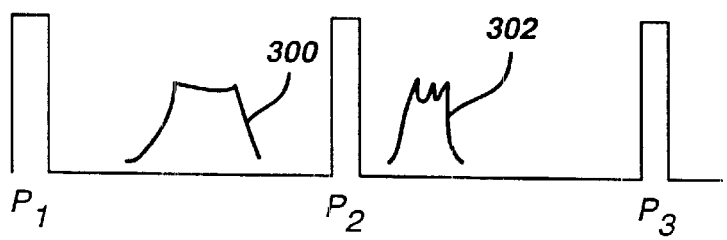
Figure 17C:
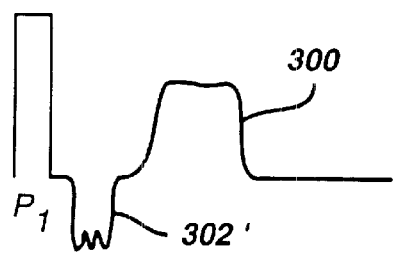

Another transmission technique which affords high pulse rates (PRF) is illustrated in FIGS. 17a–17c. FIG. 17a illustrates the transmission of a first pulse $P_1$ for contrast agent imaging of the heart, followed by a second pulse $P_2$. In this example the pulses are transmitted at a low PRF, and a significant period of time exists between the transmission times of the pulses. During this time echoes 300 are first received from contrast agent in the myocardium, and later echoes 302 are received from the more distant pericardium. Differentiation of the echoes following the two pulses will detect the presence of contrast agent in the myocardium, followed by detection of the pericardium itself.

For procedures where it is only desirable to perform contrast agent imaging of the myocardium, a higher PRF transmission can be employed as shown in FIG. 17b. The higher PRF pulses have the unfortunate result of artifact development. Echoes 300 return from the contrast agent in the myocardium following pulse $P_1$. But echoes 302 returning from the pericardium in response to the first pulse $P_1$ appear in the interval following the second pulse $P_2$ and can manifest themselves as an artifact in the image when echoes following the two pulses are differentiated. To eliminate the artifact from the later returning echoes, incoherent detection is employed prior to differentiation by the apparatus of FIG. 1. As shown in FIG. 17c, incoherent detection and differentiation results in positive polarity echoes 300' from the myocardium microbubbles, and negative polarity echoes 302' from the pericardium. The unwanted negative polarity echoes 302' from the pericardium can then be removed by thresholding or clipping at the baseline, leaving only the desired detection of the contrast agent in the myocardium.

What is claimed is:

1. A method for ultrasonically detecting the perfusion rate of tissue by ultrasonic contrast agents comprising:

introducing an ultrasonic contrast agent of microbubbles into the bloodstream;

transmitting an ultrasonic pulse which significantly disrupts microbubbles in said tissue; and following the significant disruption of said microbubbles, ultrasonically measuring the degree of microbubble replenishment of said tissue by acquiring echoes in response to substantially nondestructive pulses repetitively triggered or gated in relation to the heart cycle.

2. The method of claim 1, wherein ultrasonically measuring further comprises measuring the degree of contrast agent replenishment at a substantially constant point in the heart cycle.

3. The method of claim 2, wherein ultrasonically measuring further comprises acquiring echoes in response to pulses triggered or gated in synchronization with the diastolic phase of the heart cycle.

4. The method of claim 1, further comprising utilizing the acquired echo information to produce an ultrasonic image of the perfusion rate of tissue in a region of the body.

5. The method of claim 4, wherein producing an ultrasonic image further comprises displaying a portion of the region which is fed from a stenotic blood supply with a different degree of contrast agent reinfusion than a portion of the region which is not fed from a stenotic blood supply.

6. The method of claim 5, wherein displaying a portion of the region which is fed from a stenotic blood supply with a different degree of contrast agent reinfusion further comprises displaying a portion of the region which is fed from a stenotic blood supply with a different perfusion rate than a portion of the region which is not fed from a stenotic blood supply.

7. A method for ultrasonically measuring the perfusion rate of tissue by ultrasonic contrast agents comprising:

introducing an ultrasonic contrast agent of microbubbles into the bloodstream;

transmitting a chirp or multifrequency ultrasonic pulse which significantly disrupts microbubbles in said tissue; and following the significant disruption of said microbubbles, ultrasonically measuring the degree of microbubble replenishment of said tissue.

8. The method of claim 7, wherein the transmitted pulse is a frequency modulated pulse.

* * * * *